United States Patent [19]

Ono et al.

[11] 4,360,457

[45] Nov. 23, 1982

[54] S-SULFONATED IMMUNOGLOBULIN COMPOSITION HAVING A HIGH MONOMER CONTENT AND A PROCESS FOR PRODUCTION THEREOF

[75] Inventors: Syoji Ono, Kodaira; Yuji Fukumoto, Hino; Tsunemasa Yoshida, Hachioji, all of Japan

[73] Assignees: Teijin Limited, Osaka; The Chemo-Sero-Therapeutic Research Institute, Kumamoto, both of Japan

[21] Appl. No.: 182,053

[22] Filed: Aug. 28, 1980

[30] Foreign Application Priority Data

Aug. 30, 1979 [JP] Japan ................... 54-109644
Aug. 30, 1979 [JP] Japan ................... 54-109645
Oct. 17, 1979 [JP] Japan ................... 54-132786

[51] Int. Cl.$^3$ ............................... C07G 7/00
[52] U.S. Cl. .......................... 260/112 B; 424/85; 424/101
[58] Field of Search ............... 260/112 B; 424/85, 101

[56] References Cited

U.S. PATENT DOCUMENTS 4,059,571 11/1977 Tomibe et al. ............ 260/112 B
4,118,379 10/1978 Schmidtberger ............ 260/112 B
4,160,763 7/1979 Müller ........................ 260/112 B

OTHER PUBLICATIONS

Acta Chemica Scandinavica 22 (1968), pp. 490–496, Hansson.

*Primary Examiner*—Howard E. Schain
*Attorney, Agent, or Firm*—Sherman & Shalloway

[57] ABSTRACT

The present invention is directed to an S-sulfonated immunoglobulin composition comprising an S-sulfonated immunoglobulin and as an aggregation preventing agent or an aggregate dissociating agent, therefor, about 1 to about 600% by weight, based on the weight of the S-sulfonated immunoglobulin, of a water-soluble acid addition salt of a basic nitrogen-containing organic compound containing one or more basic nitrogen atoms in the molecule and optionally carboxyl groups smaller in number than the basic nitrogen atoms and having a pKb at 25° C. of not more than 7.

There is also provided a process for producing an S-sulfonated immunoglobulin composition having a high monomer content, which comprises contacting an S-sulfonated immunoglobulin in aqueous solution with about 1 to about 600% by weight, based on the weight of the S-sulfonated immunoglobulin, of the water-soluble acid addition salt, or reacting an immunoglobulin in aqueous solution with a compound capable of yielding a sulfite ion in water and an oxidizing agent in the presence of about 1 to about 600% by weight, based on the immunoglobulin, of the water-soluble acid addition salt.

3 Claims, No Drawings

S-SULFONATED IMMUNOGLOBULIN COMPOSITION HAVING A HIGH MONOMER CONTENT AND A PROCESS FOR PRODUCTION THEREOF

This invention relates to an S-sulfonated immunoglobulin composition having a high monomer content, and to a process for production thereof.

Immunoglobulins are of great medical significance as agents responsible for humoral immunity, and have immune activity against various pathogenic microorganisms. Administration of immunoglobulins can therefore lead to the prevention and treatment of viral infections such as measles and viral hepatitis and of infections caused by antibiotic-resistant bacteria such as staphylococci. In such prevention and treatment, intravenous injection is preferred to intramuscular injection in order to administer large amounts of an immunoglobulin and cause it to produce a rapid effect. However, intravenous administration of an immunoglobulin fractionated from human plasma may cause anaphylactic side-effects involving hypotension, chill and pyrexia, dyspnea, headache, etc. This is because aggregated immunoglobulin molecules in the immunoglobulin fractionated from human plasma combine with complements in the blood to activate them and thereby liberate biologically active factors such as an anaphylatoxin-like substance or a vasular-permeable factor.

Such aggregated immunoglobulins are inherently contained in the immunoglobulins fractionated from human plasma, and tend to form gradually with the passage of time during their formulation into dosage forms.

Various methods have been suggested for removing or alleviating these side-effects induced by aggregated immunoglobulin molecules. For example, U.S. Pat. No. 4,059,571 discloses a method for producing an intravenously injectable S-sulfonated immunoglobulin having reduced anti-complement activity while retaining various antibody activities, which comprises reacting an immunoglobulin with sodium sulfite and sodium tetrathionate to cleave SS linkages between the peptide chains of the immunoglobulin and S-sulfonate them. This method is considered to be best among the prior suggested methods.

S-sulfonation of an immunoglobulin does not lead to complete removal of aggregated immunoglobulin molecules. The reduced anticomplement activity of the resulting S-sulfonated immunoglobulin is presumably because the aggregated molecules contained in the immunoglobulin are S-sulfonated as is the monomer.

The S-sulfonated immunoglobulin containing aggregated molecules has lower anticomplement activity and is safer than an immunoglobulin containing aggregated molecules. The aggregated molecules, even when S-sulfonated, still have the ability to combine with complements. Accordingly, an S-sulfonated immunoglobulin containing a relatively large amount of aggregated molecules may possibly induce the aforesaid anaphylactice side-effects.

An S-sulfonated immunoglobulin produced in the aforesaid manner from an immunoglobulin having a relatively small amount of aggregated molecules is not likely to induce the aforesaid side-effects. Since, however, a commercially available immunoglobulin, for example, an immunoglobulin obtained by the Cohn's ethanol fractionating method, contains a relatively large amount of aggregated molecules, an S-sulfonated immunoglobulin obtained by directly S-sulfonating such an immunoglobulin does not have a sufficiently reduced anticomplement activity, and its safety in intravenous injection is still desired to be improved.

A method has previously been known which comprises adding a polymeric substance such as polyethylene glycol, a salt such as ammonium sulfate, acrinol, etc. to a solution of an immunoglobulin to precipitate the aggregated immunoglobulin molecules. It may be possible to apply this method to an S-sulfonated immunoglobulin containing aggregated molecules in an attempt to remove the aggregated molecules. Application of this method to the S-sulfonated immunoglobulin results in removal of a large amount of monomer together with the aggregated molecules. Accordingly, in view of the fact that immunoglobulins are obtained from valuable human blood, one cannot but hesitate to use this method in removing the aggregated molecules from an S-sulfonated immunoglobulin.

A method is also known which comprises treating an immunoglobulin with an acidic aqueous solution having a pH of 4 to dissociate the aggregated immunoglobulin molecules [see Acta Chemica Scandinavica, vol. 22, pages 490–496 (1968)]. When this method is applied to an S-sulfonated immunoglobulin, it is necessary to render the treating solution neutral after the treatment in order to avoid denaturation of the treated S-sulfonated immunoglobulin. In neutrality, however, the dissociated S-sulfonated immunoglobulin again aggregates as is the case with an immunoglobulin.

It is an object of this invention to provide an S-sulfonated immunoglobulin composition having a high monomer content.

Another object of this invention is to provide an S-sulfonated immunoglobulin composition which contains aggregated molecules only in such a low content as to provide low anticomplement activity suitable for intravenous injection, and which can be safely used by itself for intravenous injection.

Still another object of this invention is to provide an S-sulfonated immunoglobulin composition having excellent storage stability which does not substantially form aggregated molecules on long-term storage.

A further object of this invention is to provide an S-sulfonated immunoglobulin having a high monomer content by dissociating the aggregated molecules of the S-sulfonated immunoglobulin or preventing aggregation of the monomer of the S-sulfonated immunoglobulin.

Other objects and advantages of this invention will become apparent from the following description.

These objects and advantages of this invention are achieved in accordance with this invention by an S-sulfonated immunoglobulin composition comprising an S-sulfonated immunoglobulin and as an aggregation preventing agent or an aggregate dissociating agent therefor, about 1 to about 600% by weight, based on the weight of the S-sulfonated immunoglobulin, of a water-soluble acid addition salt of a basic nitrogen-containing organic compound containing one or more basic nitrogen atoms in the molecule and optionally carboxyl groups smaller in number than the basic nitrogen atoms and having a pKb at 25° C. of not more than 7.

According to another aspect, these objects and advantages are achieved in accordance with this invention by a process for producing an S-sulfonated immunoglobulin having a high monomer content, which comprises contacting an S-sulfonated immunoglobulin in aqueous solution with about 1 to about 600% by weight, based on the weight of the S-sulfonated immunoglobulin, of a water-soluble acid addition salt of a basic nitrogen-containing organic compound containing one or more basic nitrogen atoms in the molecule and optionally carboxyl groups smaller in number than the basic nitrogen atoms and having a pKb at 25° C. of not more than 7 thereby to prevent aggregation of the monomer of the S-sulfonated immunoglobulin, and when the S-sulfonated immunoglobulin contains aggregated molecules, dissociating them into monomers, and if desired, lyophilizing the resulting product.

According to still another aspect, these objects and advantages are achieved in accordance with this invention by a process for producing an S-sulfonated immunoglobulin having a high monomer content, which comprises reacting an immunoglobulin in aqueous solution with a compound capable of yielding a sulfite ion in water and an oxidizing agent in the presence of about 1 to about 600% by weight, based on the weight of the S-sulfonated immunoglobulin, of a water-soluble acid addition salt of a basic nitrogen-containing organic compound containing one or more basic nitrogen atoms in the molecules and optionally carboxyl groups smaller in number than the basic nitrogen atoms and having a pKb at 25° C. of not more than 7.

The S-sulfonated immunoglobulin used in this invention denotes a product obtained by cleaving interchain SS linkages of a native immunoglobulin and S-sulfonating them.

The S-sulfonated immunoglobulin can be produced, for example, by reacting an immunoglobulin composed mainly of gamma-globulin obtained from the serum, plasma and other body fluids or extracts of organs by a known method such as the ethanol fractionating method of Cohn et al. [E. G. Cohn et al., J. Am. Chem. Soc., 68, 459 (1946)] with, for example, sodium sulfite and sodium tetrathionate or sodium trithionate by the method disclosed in U.S. Pat. No. 4,059,571. Accordingly, the specification of U.S. Pat. No. 4,059,571 is hereby cited as reference.

The immunoglobulin may be used as fractionated by the aforesaid Cohn's method without purification (such an immunoglobulin usually contains at least 20% by weight of aggregated immunoglobulin molecules having a sedimentation constant of at least 9S). Or after fractionation, the immunoglobulin may be purified by purifying methods known in the art, such as treatment at pH 4, salting out, treatment with acrinol, or ion-exchange chromatography to reduce the content of aggregated immunoglobulin molecules to varying degrees, and sometimes to substantially zero.

The S-sulfonated immunoglobulin thus obtained may be used as such or after it is purified by known methods such as treatment at pH 4, salting out, treatment with acrinol or ion exchange chromatography.

The basic nitrogen-containing organic compound used in this invention contains one or more basic nitrogen atoms in the molecule and has a pKb at 25° C. of not more than 7. It may contain carboxyl groups which are smaller in number than the basic nitrogen atoms so long as the compound shows basicity.

As is well known, pKb used herein is a dissociation index of a basic compound which is defined by the following formula pKb = −log K wherein $K=[BH+]/[B]\cdot[H+]$ in which [B] is the concentration of the basic compound (i.e. the basic nitrogen-containing organic compound), [H+] is the hydrogen ion concentration, and [BH+] is the concentration of a conjugated acid.

Examples of suitable basic nitrogen-containing organic compounds which can be used in this invention include lower alkylamines, 5- or 6-membered heterocyclic compounds having 1 to 3 nitrogen atoms, guanidines optionally substituted by lower alkyl groups, lower alkyl- or aryl-amidines, basic amino acids, esters or amides of neutral amino acids at the carboxyl group, and amine derivatives of glucose. These basic nitrogen-containing organic compounds can be used either singly or in combination with each other.

Specific examples of the lower alkylamines are primary lower alkylamines such as methylamine, ethylamine, propylamine and butylamine, secondary lower alkylamines such as dimethylamine, diethylamine, dipropylamine and dibutylamine and tertiary lower alkylamines such as trimethylamine, triethylamine, tripropylamine and tributylamine. Preferably, the lower alkyl group in the lower alkylamines has 1 to 4 carbon atoms.

Specific examples of the 5- or 6-membered heterocyclic compounds having 1 to 3 nitrogen atoms include pyrrolidine, piperidine, imidazole, pyrazole and triazole. These compounds may be substituted with an alkyl group having 1 to 4 carbon atoms (such as 2-methylimidazole).

Specific examples of the optionally substituted guanidines are guanidine and methylguanidine. Preferably, the substituent alkyl group has 1 to 4 carbon atoms.

Specific examples of the amidines are $C_1$–$C_4$ alkyl amidines such as methylamidine, and benzamidines optionally substituted with a $C_1$–$C_4$ alkyl group, such as methylbenzamidine.

Examples of the basic amino acids are lysine, ornithine, arginine, hydroxylysine and histidine.

Specific examples of the esters or amides of neutral amino acids include esters formed between neutral amino acids such as glycine, alanine, valine, leucine, isoleucine, cysteine, cystine and methionine and alcohols, for example aliphatic alcohols having 1 to 4 carbon atoms such as methanol, ethanol, n-propanol and n-butanol, and amides formed between these neutral amino acids and primary or secondary amines having a $C_1$–$C_4$ alkyl group or ammonia, such as glycinamide, alaninamide and leucinamide.

The amine derivatives of glucose are, for example, compounds resulting from substitution of an amino group for at least one of the hydroxyl groups of glucose, such as D-glucosamine.

The basic nitrogen-containing organic compound is used in the form of a water-soluble acid addition salt in this invention. The water-soluble acid addition salt can be favorably prepared by using a mineral acid such as hydrochloric acid, hydrobromic acid, phosphoric acid or sulfuric acid or an organic carboxylic acid such as acetic acid. The mineral acid salts are preferred. Especially preferred are the mineral acid salts, above all hydrochlorides, of arginine, guanidine, leucinamide, imidazole, 2-methylimidazole and D-glucosamine.

The S-sulfonated immunoglobulin composition of this invention contains about 1 to about 600% by weight, preferably 10 to 600% by weight, more preferably 20 to 400% by weight, based on the S-sulfonated immunoglobulin, of the water-soluble acid addition salt of the basic nitrogen-containing organic compound. If the amount of the water-soluble acid addition salt is less than about 1% by weight, the effect of this compound to dissociate the aggregated S-sulfonated immunoglobulin molecules and prevent re-aggregation of the molecular chains of the S-sulfonated immunoglobulin becomes so small as to deviate from the range intended by the present invention. If, on the other hand, it exceeds about 600% by weight, the intended effect can be obtained but economic or operational disadvantages arise.

The S-sulfonated immunoglobulin composition of this invention contains the water-soluble acid addition salt of the basic nitrogen-containing organic compound as an aggregation preventing agent or as an aggregate dissociating agent for the S-sulfonated immunoglobulin. The water-soluble acid addition salt serves to dissociate the aggregated S-sulfonated immunoglobulin molecules and prevent aggregation of the molecules of the S-sulfonated immunoglobulin.

The essence of this invention lies in the provision of an S-sulfonated immunoglobulin composition which has a low content of aggregated molecules and therefore a high monomer content.

Since the S-sulfonated immunoglobulin composition provided by this invention has a low aggregate content and a very low anticomplement activity, it encompasses a composition which is intravenously injectable while containing a water-soluble acid addition salt of a basic nitrogen-containing organic compound such as L-arginine hydrochloride. For example, a composition in accordance with this invention comprising an S-sulfonated immunoglobulin and about 10 to about 100% by weight, based on the S-sulfonated immunoglobulin, of L-arginine hydrochloride is preferably used for this purpose.

The S-sulfonated immunoglobulin composition provided by this invention also encompasses a composition which cannot be used by itself for intravenous injection and which can be regarded as an intermediate composition for the production of an intravenously injectable S-sulfonated immunoglobulin preparation.

This intermediate composition in accordance with this invention can be formed into an S-sulfonated immunoglobulin preparation suitable for intravenous injection by removing the water-soluble acid addition salt of a basic nitrogen-containing organic compound therein by dialysis, etc. in a step as close as possible to the final step of lyophilization in the drug formulating process, and then lyophilizing the residue.

Such an S-sulfonated immunoglobulin composition can be provided by contacting an S-sulfonated immunoglobulin containing aggregated molecules with the water-soluble acid addition salt; or contacting a purified S-sulfonated immunoglobulin substantially free from aggregated molecules with the water-soluble acid addition salt; or preparing an S-sulfonated immunoglobulin from an immunoglobulin containing aggregated molecules in the presence of the water-soluble acid addition salt.

Thus, according to this invention, there is first provided a process for producing an S-sulfonated immunoglobulin composition having a higher monomer content, which comprises contacting an S-sulfonated immunoglobulin containing aggregated molecules in aqueous solution with about 1 to about 600% by weight, based on the S-sulfonated immunoglobulin, of at least one water-soluble acid addition salt of a basic nitrogen-containing organic compound containing one or more basic nitrogen atoms in the molecule and optionally carboxyl groups smaller in number than the basic nitrogen atoms and having a pKb at 25° C. of not more than 7 thereby to prevent aggregation of the monomer of the S-sulfonated immunoglobulin and to dissociate the aggregated molecules into monomers, and then if desired, lyophilizing the resulting product.

Secondly, there is provided a process for producing an S-sulfonated immunoglobulin composition having a high monomer content, which comprises contacting a purified S-sulfonated immunoglobulin substantially free from aggregated molecules with the same amount as above of at least one aforesaid water-soluble acid addition salt in aqueous solution thereby to prevent aggregation of the monomer of the S-sulfonated immunoglobulin, and then if desired, lyophilizing the resulting product.

Thirdly, the invention provides a process for producing an S-sulfonated immunoglobulin composition having a high monomer content, which comprises reacting an immunoglobulin in aqueous solution with a compound capable of yielding a sulfite ion in water and an oxidizing agent in the presence of about 1 to about 600% by weight, based on the weight of the immunoglobulin, of at least one aforesaid water-soluble acid addition salt.

In the first and second processes of this invention, the S-sulfonated immunoglobulin and the water-soluble acid addition salt of a basic nitrogen-containing organic compound are contacted with each other in aqueous solution. The contacting is effected at a temperature of about 0° to about 50° C., preferably about 0° to about 30° C. Desirably, the pH of the aqueous solution during contacting is about 5 to about 8.

The greatest characteristic of the process of this invention is that as seen in the second process as soon as the aggregated S-sulfonated immunoglobulin molecules in the starting S-sulfonated immunoglobulin are contacted with the water-soluble acid addition salt under the aforesaid contacting conditions, dissociation of the aggregated molecules begins, and within a period of as short as 1 hour, dissociation of the aggregated S-sulfonated immunoglobulin molecules can be substantially achieved and thereby an S-sulfonated immunoglobulin having a high monomer content can be provided.

A second feature of the process of this invention is that as typically expressed by the second process, even when the contacting is continued for a period longer than the aforesaid time, substantial dissociation of the aggregated S-sulfonated immunoglobulin molecules is retained over a long period of time.

The first and second processes in accordance with this invention can be practiced by directly adding the water-soluble acid addition salt to a solution of the S-sulfonated immunoglobulin, or by mixing a solution of the S-sulfonated immunoglobulin with a solution of the water-soluble acid addition salt.

In the latter-mentioned procedure, the water-soluble acid addition salt may be produced in situ by preparing an aqueous solution of the basic nitrogen-containing organic compound and adding an acid such as hydrochloric acid to the aqueous solution to adjust its pH to about 5 to about 8.

According to the process of this invention, the resulting aqueous solution of S-sulfonated immunoglobulin having a high monomer content, if required, can be lyophilized by a method known per se to provide the composition of this invention in the form of a lyophilized solid. Preferably, the composition of this invention provided in the form of a lyophilized solid is an intravenously injectable composition comprising a non-toxic water-soluble acid addition salt capable of being used in intravenous injection. Such an intravenously injectable composition is dissolved in sterilized water or physiological saline to form an intravenous injecting preparation.

Preferably, the composition of this invention provided in the form of a lyophilized solid contains about 1 to about 100% by weight, based on the weight of the immunoglobulin, of a nontoxic water-soluble acid addition salt such as L-arginine hydrochloride.

The sulfonation reaction in the third process of this invention is carried out in water. The pH of the reaction system during the reaction is preferably in the range of 5.0 to 9.0. The reaction temperature is from 0° to 50° C., preferably from 10° to 45° C. At a temperature of more than 50° C., the immunoglobulin molecules are undesirably susceptible to denaturation. At a temperature of less than 0° C., the reaction proceeds too slowly to be commercially feasible. The reaction is continued until almost all of the interchain SS linkages of the immunoglobulin are cleaved and S-sulfonated. The reaction time, which varies depending upon the amounts of the reagents, the reaction temperature, etc., is generally from 0.5 to 24 hours.

Suitable oxidizing agents are those which have low reactivity with a sulfite ion generated from the other reagent. Examples of the oxidizing agents are compounds capable of forming a polythionate ion having 3 to 6 sulfur atoms, such as a trithionate ion, a tetrathionate ion, a pentathionate ion or a hexathionate ion, in water (e.g., the sodium, potassium or ammonium salt of a polythionic acid having 3 to 6 sulfur atoms); compounds capable of forming a cupric ion in water (e.g., cupric chloride, cupric bromide or cupric sulfate); compounds capable of forming an iodobenzoate ion in water (e.g., the sodium, potassium or ammonium salt of iodobenzoic acid); and molecular oxygen-containing gases such as water (in this case, the gases desirably contain a catalytic amount of cysteine or 2-mercaptoethylamine).

Examples of the compound capable of yielding a sulfite ion in water include sulfurous acid salts such as sodium sulfite, potassium sulfite and ammonium sulfite; bisulfites such as sodium bisulfite, potassium bisulfite and ammonium bisulfite; and pysobisulfites such as sodium pyrobisulfite, potassium pyrobisulfite and ammonium pyrobisulfite.

The amount of the compound capable of yielding a sulfite ion in water is at least 2 moles, preferably at least 10 moles, per mole of the interchain SS linkage of the immunoglobulin to be cleaved. The amount of the oxidizing agent is at least 1 mole, preferably at least 2 mole, per mole of the interchain SS linkage of the immunoglobulin to be cleaved.

The water-soluble acid addition salt of a basic nitrogen-containing organic compound to be present in the reaction system may be added to the reaction system as such a salt or as a basic nitrogen-containing organic compound. When it is added as a basic nitrogen-containing compound, it reacts with an acid such as sulfurous acid present in the reaction system to change to its water-soluble acid addition salt.

The basic nitrogen-containing organic compound or its water-soluble acid addition salt is added prior to the sulfonation reaction to the reaction system in an amount of about 1 to about 600% by weight, preferably 10 to 600% by weight, more preferably 20 to 400% by weight, based on the immunoglobulin. When the amount of the basic nitrogen-containing organic compound is less than 1% by weight, the effect of the invention cannot be sufficiently obtained. If it exceeds 600% by weight, the effect of this invention can be obtained, but economical or operational disadvantages arise. The temperature at which the basic nitrogen containing organic compound is added is from 0° to 50° C., preferably from 0° to 30° C.

According to the third process, dissociation of the aggregated molecules of the resulting S-sulfonated immunoglobulin in the reaction system proceeds simultaneously with the S-sulfonation reaction of the immunoglobulin.

In the S-sulfonated immunoglobulin formed in the reaction system, the H chain-H chain and H chain-L chain of the immunoglobulin are mostly cleaved, but the three-dimensional structure of the immunoglobulin is substantially retained by a non-covalent bond such as hydrogen bond between the chains.

The S-sulfonated immunoglobulin is generally separated from the reaction system by using a purifying method such as dialysis, salting out or column chromatography. For example, by dialyzing the resulting reaction solution with a physiological saline, a solution of the final product in physiological saline is obtained.

As can be appreciated from the foregoing, the process of this invention includes the following embodiments so long as the aggregated S-sulfonated immunoglobulin molecules can be substantially dissociated and aggregation of the S-sulfonated immunoglobulin molecules is substantially inhibited.

(1) A process comprising contacting an S-sulfonated immunoglobulin (obtained by S-sulfonating by, for example, the method described in U.S. Pat. No. 4,059,571 an immunoglobulin containing at least about 20% by weight of aggregated molecules and prepared by the Cohn's ethanol fractionating method) with the water-soluble acid addition salt in aqueous solution. If the S-sulfonated immunoglobulin is provided as a lyophilized product, it is used as an aqueous solution. The lyophilized S-sulfonated immunoglobulin contains aggregated molecules. However, a solid mixture of such a solid S-sulfonated immunoglobulin and a predetermined amount of the water-soluble acid addition salt should be understood as constituting part of the S-sulfonated immunoglobulin composition of this invention because by converting it into an aqueous solution, substantial dissociation of the aggregated S-sulfonated immunoglobulin molecules can be achieved.

(2) A process comprising contacting an S-sulfonated immunoglobulin (obtained by S-sulfonating by, for example, the method described in U.S. Pat. No. 4,059,571, an immunoglobulin treated with an acid by the method of Hanson et al. [Acta Chemica Scandinavica, vol. 22, pages 490-496 (1968)]) with the water-soluble acid addition salt in aqueous solution. When the immunoglobulin treated with an acid by the method of Hanson et al. is adjusted to a pH near neutrality, the immunoglobulin molecules again aggregate. Moreover, when the immunoglobulin is maintained at a pH of about 4 for a long period of time, it undergoes denaturation. In this case, it is desirable to use an immunoglobulin which is acid-treated at a time as close as possible to the performance of the sulfonation reaction.

(3) A process comprising contacting a purified S-sulfonated immunoglobulin substantially free from aggregated molecules with the water-soluble acid addition salt in aqueous solution.

(4) A process comprising S-sulfonating in accordance with the method described in U.S. Pat. No. 4,059,571 an immunoglobulin obtained by the Cohn's ethanol fractionating method or an immunoglobulin acid-treated by the method of Hanson et al. in the presence of the water-soluble acid addition salt, whereby the S-sulfonated immunoglobulin formed in the S-sulfonation reaction system is contacted with the water-soluble acid addition salt.

The present invention provides the following types of composition.

(1) An S-sulfonated immunoglobulin composition being substantially free from aggregated molecules and being in the form of an aqueous solution capable of being directly used for intravenous injection.

(2) An S-sulfonated immunoglobulin composition in the form of a lyophilized solid which does not substantially contain aggregated molecules and can be used as an intravenous injecting preparation by being formed into an aqueous solution.

(3) An S-sulfonated immunoglobulin composition which does not substantially contain aggregated molecules but is in the form of an aqueous solution which cannot be directly used as an intravenously injectable preparation. An intravenously injectable S-sulfonated immunoglobulin preparation can be prepared by removing the water-soluble acid addition salt from this composition not suitable for intravenous injection.

As can be appreciated from the detailed description above, the process of this invention makes it possible to dissociate the aggregated molecules of an S-sulfonated immunoimmunoglobulin, and to prevent aggregation of the S-sulfonated immunoglobulin molecules. Accordingly, the invention also brings about the excellent advantage that aggregated molecules can be utilized as dissociated S-sulfonated immunoglobulins which can be intravenously injected.

The following Examples and Comparative Examples illustrate the present invention in detail. All percentages in these examples are by weight.

In these examples, measurement of the monomer content and the anticomplement activity of an S-sulfonated immunoglobulin and sodium dodecylsulfate (SDS) disc electrophoresis were performed by the following methods.

Monomer content of S-sulfonated immunoglobulin

The content of monomers (sedimentation constant 7 S; molecular weight about 160,000) is determined by subjecting 0.3 ml of a 5% aqueous solution of an S-sulfonated immunoglobulin to gel-filtration analysis. Sepharose CL-6B (Pharmacia Co.) is used as a gel, and a column having a diameter of 1.5 cm and a length of 80 cm is used. The rate of flow of the solution is 0.17 ml/min.

Anticomplement activity

A 1% S-sulfonated immunoglobulin (GVB++) solution (5ml) containing guinea pig serum, 20 $CH_{50}$/ml. is incubated at 37° C. for an hour, and the consumed complement is measured by the method described in Kabat & Mayer, "Experimental Immunochemistry", page 225, 1961. The anticomplement activity levels are indicated by the percentage of consumption to 20 $CH_{50}$/ml.

SDS disc electrophoresis

The resulting S-sulfonated immunoglobulin is subjected to SDS disc electrophoresis by the method of Weber and Osborne [J. Biol. Chem. 244, 4406 (1969)] to determine the amount of the unreacted immunoglobulin.

EXAMPLES 1 to 10 and COMPARATIVE EXAMPLES 1 to 4

A solution of 7.5 g of sodium tetrathionate in 50 ml of a 0.1 M phosphate buffer containing sodium chloride and having a pH of 7.2 and a solution of 12.3 g of sodium sulfite in 100 ml of a 0.1 M phosphate buffer containing sodium chloride and having a pH of 7.2 were added to 300 ml of a 15% solution of human immunoglobulin (fraction II obtained by the method of Cohn's ethanol fractionating method), and they were reacted at 42° C. for 4.5 hours. After the reaction, the reaction mixture was cooled with ice, and dialyzed against a 0.9% aqueous solution of sodium chloride to obtain a solution of an S-sulfonated immunoglobulin.

A predetermined amount of each of the additive shown in Table 1 (water-soluble acid addition salts of basic nitrogen-containing organic compounds having a pKb of not more than 7 in accordance with this invention or comparative compounds) was mixed with 10 ml of a 5% solution of the resulting S-sulfonated immunoglobulin. One hour after the addition and on standing at 4° C. for 3 weeks, the monomer content and anticomplement activity of the S-sulfonated immunoglobulin were measured. The results are shown in Table 1.

TABLE 1

| Example (Ex.) or Comparative Example (CEx.) | Additive | | | One hour later | | On standing for 3 weeks | |
|---|---|---|---|---|---|---|---|
| | Type | $pKb^{25}$ | Amount (g) | Monomer content (%) | Anti-complement activity | Monomer content (%) | Anti-complement activity |
| Ex. 1 | L-arginine hydrochloride | 1.52 | 0.25 | 83.8 | 18.5 | 83.2 | 19.0 |
| Ex. 2 | " | 1.52 | 0.5 | 88.6 | 9.6 | 87.9 | 10.2 |
| Ex. 3 | " | 1.52 | 1 | 91.2 | 7.2 | 90.9 | 7.7 |
| Ex. 4 | L-lysine hydrochloride | 3.47 | 1 | 85.9 | 15.3 | 86.3 | 16.4 |
| Ex. 5 | L-leucinamide hydrochloride | 4.40 | 1 | 90.7 | 8.6 | 90.5 | 8.8 |
| Ex. 6 | Guanidine hydrochloride | 0.6 | 1 | 91.4 | 7.7 | 91.7 | 8.6 |
| Ex. 7 | Triethylamine hydrochloride | 3.28 | 1 | 86.5 | 17.3 | 85.4 | 17.9 |
| Ex. 8 | D-glucosamine hydrochloride | — | 0.5 | 87.2 | 16.2 | 87.3 | 17.1 |
| Ex. 9 | Imidazole hydrochloride | 6.97 | 1 | 89.3 | 10.3 | 88.9 | 10.0 |
| Ex. 10 | 2-Methylimidazole | | | | | | |

TABLE 1-continued

| Example (Ex.) or Comparative Example (CEx.) | Additive | | | One hour later | | On standing for 3 weeks | |
|---|---|---|---|---|---|---|---|
| | Type | pKb[25] | Amount (g) | Monomer content (%) | Anti-complement activity | Monomer content (%) | Anti-complement activity |
| | hydrochloride | 6.55 | 1 | 90.1 | 9.8 | 91.2 | 10.3 |
| CEx. 1 | None | — | 0 | 76.5 | 26.6 | 70.8 | 32.0 |
| CEx. 2 | Glycine | — | 1 | 76.5 | 28.2 | 73.6 | 27.5 |
| CEx. 3 | Glucose | — | 1 | 80.2 | 25.0 | 78.6 | 26.0 |
| CEx. 4 | Albumin | — | 0.1 | 78.6 | 24.3 | 75.4 | 26.3 |

It is seen from Table 1 that the S-sulfonated immunoglobulin compositions obtained by adding water-soluble salts of basic nitrogen-containing organic compounds having a pKb at 25° C. of not more than 7 (Examples 1 to 10) have a higher monomer content and a much lower anticomplement activity than the comparative compositions (comparative Examples 1 to 4) because the aggregated S-sulfonated immunoglobulin molecules are dissociated, and that this state is substantially retained even after a lapse of 3 weeks.

EXAMPLE 11

A 10% solution of the same S-sulfonated immunoglobulin as used in Example 1 was purified by salting out with sodium sulfate, and one gram of L-arginine hydrochloride was added to 10 ml of a 5% solution of the purified S-sulfonated immunoglobulin. The mixture was allowed to stand at 4° C. for 1 week. The resulting composition had a monomer content of 93.0% and an anticomplement acitivity of 3.5. When L-arginine hydrochloride was not added, the S-sulfonated immunoglobulin showed an anticomplement acitivity of 17.6 and a monomer content of 78.5% after standing for 1 week at 4° C.

EXAMPLE 12

A 10% solution of the same S-sulfonated immunoglobulin as used in Example 1 was purified with acrinol. One gram of L-arginine hydrochloride was added to 10 ml of a 5% solution of the purified S-sulfonated immunoglobulin, and the mixture was allowed to stand at 4° C. for one week. The composition showed an anticomplement activity of 2.7 and a monomer content of 91.9%. When L-arginine hydrochloride was not added, the S-sulfonated immunoglobulin showed an anticomplement activity of 15.1 and a monomer content of 77.5% on standing at 4° C. for 1 week.

EXAMPLES 13 to 17 and COMPARATIVE EXAMPLES 5 to 7

Ten milliliters of a 10% solution of the same S-sulfonated immunoglobulin as used in Example 1 was dialyzed with a 0.1 M acetate buffer having a pH of 4, and treated with an acid in accordance with the method of Hanson et al. [see Acta Chemica Scandinavica, vol. 22, pages 490–496 (1968)]. The treated S-sulfonated immunoglobulin was then dialyzed against a 0.05 M phosphate buffer containing 0.5 M sodium chloride (pH 7.0) to neutralize it and to obtain 12.5 ml of a solution of the S-sulfonated immunoglobulin (concentration 7.6%).

A predetermined amount of each of the additive (water-soluble salts of basic nitrogen-containing organic compounds having a pKb at 25° C. of not more than 7 in accordance with this invention and comparative additives) shown in Table 2 was added to 10 ml of a 5% solution of the acid-treated S-sulfonated immunoglobulin. One hour after the addition and on standing at 4° C. for one week, the monomer content and anticomplement activity of the acid-treated S-sulfonated immunoglobulin were measured. The results are shown in Table 2.

TABLE 2

| Example (Ex.) or Comparative Example (CEx.) | Additive | | One hour later | | On standing for 1 week | |
|---|---|---|---|---|---|---|
| | Type | Amount (g) | Monomer content (%) | Anti-complement activity | Monomer content (%) | Anti-complement activity |
| Ex. 13 | L-arginine hydrochloride | 0.25 | 85.4 | 9.0 | 83.5 | 8.0 |
| Ex. 14 | " | 0.5 | 88.6 | 3.0 | 87.0 | 2.8 |
| Ex. 15 | " | 1 | 90.4 | 1.0 | 90.5 | 0.6 |
| Ex. 16 | L-lysine hydrochloride | 1 | 86.6 | 10.3 | 86.0 | 11.0 |
| Ex. 17 | D-glucosamine hydrochloride | 0.5 | 88.8 | 10.1 | 87.2 | 10.3 |
| CEx. 5 | None | 0 | 85.3 | 10.6 | 77.5 | 15.1 |
| CEx. 6 | Glycine | 1 | 86.2 | 10.6 | 79.2 | 15.2 |
| CEx. 7 | Glucose | 1 | 84.7 | 11.0 | 80.2 | 14.8 |

It is seen from Table 2 that in the S-sulfonated immunoglobulin compositions obtained by adding the water-soluble salts of basic nitrogen-containing organic compounds having a pKb of not more than 7 at 25° C. (Examples 13 to 17), the formation of aggregated molecules is inhibited, and their anticomplement activities are maintained low, over a longer period of time than in the case of the comparative compositions.

EXAMPLE 18

L-arginine hydrochloride (1.5 g) was added to 30 ml of a 10% solution of human immunoglobulin (fraction II obtained by the Cohn's ethanol fractionating method; monomer content 76.2%; anticomplement activity less than 90; antibody value diphtheria 2.0 units/ml). To the resulting solution were added a solution of 0.5 g of sodium tetrathionate in 2 ml of a 0.1 M phosphate buffer containing sodium chloride (pH 7.2) and a solution of 0.82 g of sodium sulfite in 8 ml of a 0.1 M phosphate buffer containing sodium chloride (pH 7.2). Thus, the immunoglobulin was S-sulfonated at 37° C. for 4.5 hours. After the reaction, the reaction mixture was cooled with ice, and dialyzed against a 0.9% aqueous solution of sodium chloride to obtain 42 ml of a 6.5% solution of the S-sulfonated immunoglobulin. The resulting S-sulfonated immunoglobulin had the following properties.

Monomer content: 85.6%
Anticomplement activity: 9.0%
Amount of immunoglobulin ($H_2L_2$): 0.8% by SDS disc electrophoresis
Antibody value: diptheria 2.0 units/ml.

COMPARATIVE EXAMPLE 8

By operating under the same conditions as in Example 18 except that L-arginine hydrochloride was not added, 40 ml of a 6.7% solution of the S-sulfonated immunoglobulin was obtained. The resulting S-sulfonated immunoglobulin had a monomer content of 77.1% and an anticomplement activity of 28.0.

EXAMPLE 19

By operating in the same way as in Example 18 except that 1.5 g of L-ornithine hydrochloride was used instead of L-arginine hydrochloride, 40 ml of a 6.4% solution of S-sulfonated immunoglobulin was obtained. The resulting S-sulfonated immunoglobulin had a monomer content of 84.1%.

EXAMPLE 20

By operating in the same way as in Example 18 except that 1.5 g of L-lysine hydrochloride was used instead of L-arginine hydrochloride, 41 ml of a 6.6% solution of S-sulfonated immunoglobulin was obtained. The resulting S-sulfonated immunoglobulin had a monomer content of 83.2%.

EXAMPLE 21

By operating in the same way as in Example 18 except that L-leucinamide hydrochloride was used instead of L-arginine hydrochloride, 43 ml of a 6.3% solution of S-sulfonated immunoglobulin was obtained. The resulting S-sulfonated immunoglobulin had a monomer content of 85.3%.

EXAMPLE 22

By operating in the same way as in Example 18 except that D-glucosamine hydrochloride was used instead of L-arginine hydrochloride, 42 ml of a 6.6% solution of S-sulfonated immunoglobulin was obtained. The resulting S-sulfonated immunoglobulin had a monomer content of 83.9%.

EXAMPLE 23

L-arginine hydrochloride (1.5 g) was added to 30 ml of a 10% solution of human immunoglobulin (fraction II obtained by the Cohn's ethanol fractionating method). To the resulting solution were added a solution of 0.4 g of sodium trithionate in 2 ml of a 0.1 M phosphate buffer containing sodium chloride (pH 7.2) and a solution of 0.82 g of sodium sulfite in 8 ml of 0.1 M phosphate buffer containing sodium chloride (pH 7.2). The immunoglobulin was thus S-sulfonated at 37° C. for 4.5 hours.

After the reaction, the reaction mixture was cooled with ice, and dialyzed against a 0.9% aqueous solution of sodium chloride to obtain 45 ml of a 6.0% solution of an S-sulfonated immunoglobulin. The resulting S-sulfonated immunoglobulin had a monomer content of 86.2% and an anticomplement activity of 8.7%.

What we claim is:

1. A process for producing an S-sulfonated immunoglobulin composition having a high monomer content, which comprises contacting an S-sulfonated immunoglobulin in aqueous solution with about 10 to about 600% by weight, based on the weight of the S-sulfonated immunoglobulin, of a water-soluble acid addition salt of a basic amino acid and having a pKb at 25° C. of not more than 7 at a temperature of about 0° C. to about 50° C. in the absence of freezing and at a pH of from about 5 to about 8 thereby to prevent aggregation of the monomer of the S-sulfonated immunoglobulin in the aqueous solution, and when the S-sulfonated immunoglobulin contains aggregated molecules, dissociating the aggregated molecules into monomers.

2. A process for producing an S-sulfonated immunoglobulin composition having a high monomer content, which comprises reacting an immunoglobulin in aqueous solution with a compound capable of yielding a sulfite ion in water and an oxidizing agent in the presence of about 10 to about 600% by weight, based on the immunoglobulin, of a water-soluble acid addition salt of a basic amino acid and having a pKb at 25° C. of not more than 7 at a temperature of about 0° C. to about 50° C. in the absence of freezing and at a pH of about 5 to about 8.

3. The process of claim 1 or 2 wherein the basic amino acids are lysine, ornithine and arginine.

* * * * *